| United States Patent [19] | [11] Patent Number: 4,764,466 |
| Suyama et al. | [45] Date of Patent: Aug. 16, 1988 |

[54] METHOD FOR STABILIZING AN IMMOBILIZED FIBRINOLYTIC ENZYME

[75] Inventors: Katsuhiko Suyama, Kyoto; Yasunori Yabushita, Nara; Masanao Koyama; Kunihiko Takagi, both of Kyoto, all of Japan

[73] Assignee: Unitika Ltd., Hyogo, Japan

[21] Appl. No.: 799,239

[22] Filed: Nov. 18, 1985

[30] Foreign Application Priority Data

Nov. 16, 1984 [JP] Japan ................... 59-242706

[51] Int. Cl.⁴ .................. C12N 11/00; C12N 9/96
[52] U.S. Cl. .................... 435/174; 435/176; 435/178; 435/180; 435/188
[58] Field of Search ............ 435/174, 176, 177, 178, 435/179, 180, 182, 188

[56] References Cited

U.S. PATENT DOCUMENTS 3,950,223  4/1976  Yugari et al. ............ 435/188
4,244,943  1/1981  Yamahira et al. ......... 435/188 X
4,246,349  1/1981  Chessing et al. ......... 435/174 X

OTHER PUBLICATIONS

Chibata, I., Immobilized Enzymes, John Wiley & Sons, N.Y. 1978, pp. 22, 23, 26, 27, 134–143, 216 and 217.

*Primary Examiner*—David M. Naff
*Attorney, Agent, or Firm*—Sughrue, Mion, Zinn, Macpeak, and Seas

[57] ABSTRACT

A fibrinolytic enzyme immobilized on a carrier is stabilized by treating the surface of the carrier on which the enzyme is immobilized with a basic amino acid. The amino acid is preferably histidine, arginine or lysine. Carriers may be inorganic materials, natural polymeric materials or synthetic polymeric materials, in a variety of forms. Fibrinolytic enzymes immobilized include plasmin, brinase, urokinase, streptokinase and tissue plasminogen activator. The stabilized immobilized fibrinolytic enzyme maintains activity better during storage or sterilization.

16 Claims, No Drawings

METHOD FOR STABILIZING AN IMMOBILIZED FIBRINOLYTIC ENZYME

FIELD OF THE INVENTION

The present invention relates to a method of stabilizing a fibrinolytic enzyme immobilized on a carrier.

BACKGROUND OF THE INVENTION

Fibrinolytic and thrombolytic enzymes have been extensively used in the treatment of thromboembolic vascular diseases, with remarkable clinical results. The high thrombolytic power of fibrinolytic enzymes are incorporated in anti-thrombic materials which have such enzymes immbolized on the surfaces of polymeric materials, and because of their excellent anti-thrombic activities, such materials have been found to be very useful as a variety of blood-contact materials (see, for example, *Igaku no Ayumi* (Progress of Medical Science), vol. 101, p. 144, 1971).

It has however turned out that the activities of the immobilized fibrinolytic enzymes decrease more or less with time, as in the case of unimmobilized enzymes. This limits the utility of the anti-thrombic materials in spite of their high activities because, for one thing, they cannot be stored for an extended period at room temperature, and for another, they have to be stored under special refrigerated conditions in order to prevent activity drop.

Further, anti-thrombic materials having fibrinolytic enzymes immobilized on polymeric surfaces must be sterilized before they are used in medical fields. However, enzymes are instable physiological substances and their activities can be reduced or entirely lost as a result of sterilization. The deactivation of enzymes is therefore another serious problem that must be solved before they are used in anti-thrombic materials.

Many proposals have been made with a view to enhancing the storage stability of the activity of unimmobilized fibrinolytic enzymes, and they include the use of protamine, as described in Japanese Patent Application (OPI) No. 117486/1977 (The term "OPI" as used herein refers to a "published unexamined Japanese Patent Application".); chlorhexidine or salts thereof, as described in Japanese Patent Application (OPI) No. 120186/1977; dextran sulfate and salts thereof, as described in Japanese Patent Application (OPI) Nos. 89083/1979, 34082/1980, and 145591/1977; albumin, as described in Japanese Patent Application (OPI) No. 142592/1978; sulfate esters of sugars, as described in Japanese Patent Application (OPI) No. 32691/1979; glycoproteins, such as mucin and mucoid, as described in Japanese Patent Application (OPI) No. 44004/1979; guanine and guanine derivatives, as described in Japanese Patent Application (OPI) No. 46885/1979; gelatin, as described in Japanese Patent Application (OPI) Nos. 64688/1979 and 80406/1979; chondroitin sulfate, as described in Japanese Patent Application (OPI) No. 67089/1979; hydroxyethyl starch, dextran, and nicotinamide, as described in Japanese Patent Application (OPI) No. 70419/1979; hydrodextrin sulfate, as described in Japanese Patent Application (OPI) No. 68290/1980; hydroxypropyl cellulose, as described in Japanese Patent Application (OPI) No. 23891/1981; and a compound having at least one of disulfido group and mercapto group, as described in Japanese Patent Application (OPI) No. 37882/1979.

Use of amino acids has also been proposed, such as in Japanese Patent Application (OPI) No. 142593/1978 (amino acids, sugars and neutral salts), Japanese Patent Application (OPI) No. 18486/1973 (neutral amino acids), Japanese Patent Application (OPI) No. 80284/1974 (amines, amides and ammonium ion), and Japanese Patent Application (OPI) No. 147916/1979 (human serum albumin and polar amino acids). In three of these patents, amino acids are shown to be used in combination with other compounds. In Japanese Patent Application (OPI) No. 142593/1978, glycine, lysine and arginine are mentioned as amino acids; in Japanese Patent Application (OPI) No. 80284/1974 (corresponding to U.S. Pat. No. 3,950,223), arginine (amino acid) is mentioned as an amine; and in Japanese Patent Application (OPI) No. 147916/1979 (corresponding to U.S. Pat. No. 4,244,943), polar amino acids are used together with human serum albumin, including arginine, aspartic acid, glutamic acid, histidine, lysine, serine and threonine, among which lysine, arginine and histidine are classified as basic amino acids.

As shown above, there exist a host of patents disclosing methods for enhancing the storage activities of unimmobilized fibrinolytic enzymes, but no method has been described in connection with immobilized fibrinolytic enzymes. As for the elimination or reduction of the enzymatic activity resulting from sterilization, unimmobilized fibrinolytic enzymes are generally used without sterilization, so there is no wonder that the literature is completely devoid of proposals for preventing the activities of such enzymes from being eliminated or reduced as a result of sterilization. However, immobilized fibrinolytic enzymes must be sterilized before they are used in medical fields, but no technique has been successfully developed so far in order to prevent the inactivation of such immobilized enzymes resulting from sterilization.

SUMMARY OF THE INVENTION

One object, therefore, of the present invention is to provide a method for preventing the activity of a fibrinolytic enzyme immobilized on a carrier from being decreased with time.

Another object of the present invention is to provide a method for preventing the activity of a fibrinolytic enzyme immobilized on a carrier from being decreased as a result of sterilization.

As a result of extensive research conducted with a view to attaining these objects, the present inventors have now found that the activity of a fibrinolytic enzyme immobilized on a carrier can be better maintained during storage, or as a result of sterilization, by a method comprising treating the enzyme immobilizing carrier with a basic amino acid before said enzyme immobilizing carrier is stored or sterilized. The present invention has been accomplished on the basis of this finding.

Thus, the present invention is directed to a method for stabilizing an immobilized fibrinolytic enzyme, comprising treating the surface of a carrier on which said enzyme is immobilized with a basic amino acid.

DETAILED DESCRIPTION OF THE INVENTION

The immobilized fibrinolytic enzyme to be treated by the method of the present invention may be supported on any known solid carrier. Preferred carriers are inorganics such as glass, kaolinite, bentonite and activated carbon; natural polymeric materials such as natural rubber, cellulose, starch, collagen, agarose, dextran, and proteins; and synthetic polymeric materials substances such as polystyrene, polyamides, polyesters, polyamino acids, polyethylene, polyurethane, polypropylene, silicone resins, polyvinyl chloride, polymethacrylate esters, polyvinyl alcohol, and ethylene-vinyl acetate copolymer. These carriers are not limited to any specific form, and they may assume a variety of forms such as fibers, hollow fibers, tubes, films, coatings, permeable membranes, beads, powders and other forms that can be appropriately selected depending upon the specific object.

The terminology "fibrinolytic enzyme" used in the case of the present invention refers to any enzyme that is responsible for the lysis of fibrin, as is illustrated by plasmin, brinase, urokinase, streptokinase, and tissue plasminogen activator.

These fibrinolytic enzymes may be immobilized on carriers by any known enzyme immobilizing techniques, such as those described in [Koteika Koso (Immobilized Enzymes), ed. by Ichiro Chibata, Kodansha, Mar. 20, 1975, as well as Japanese Patent Application (OPI) Nos. 88390/1978 and 26394/1979. Illustrative methods that can be used include covalent bonding, ionic bonding, and adsorption processes. In the covalent bonding process, carriers having or incorporating reactive functional groups (e.g. carboxyl, amino, chloroformyl, diazonium, azido, epoxy, formyl, bromoacetyl, isocyanato, carboxylic anhydride and imidocarbonate) are used. In the ionic bonding process, carriers having or incorporating ion-exchange groups (e.g., carboxylate, sulfonate, ammonium, sulfonium, and phosphonium) are used. In the adsorption process, activated carbon, kaolinite, bentonite, and other carriers having great affinity for enzymes are used.

The terminology "basic amino acid" used in the case of the present invention refers to any amino acid having a basic side chain. This amino acid may be in the form of its derivatives such as esters and salts. Illustrative basic amino acids that can be used in the present invention include arginine, histidine, and lysine. For the purpose of providing enhanced storage stability, histidine and its derivatives are particularly effective, and for the purpose of providing improved stability against sterilization, argine and its derivatives are particularly effective.

The basic amino acid is typically used in the form of an aqueous solution, which may optionally contain a salt or a water-miscible organic solvent. The purposes of the present invention are satisfactorily attained by treating the surface of the carrier with dilute solutions of basic amino acid. A preferred concentration of the basic amino acid solution ranges from about 0.00001 wt% to about 30 wt%, with the range of from 0.001 to 1 to wt% being particularly preferred.

The surface of the carrier on which the fibrinolytic enzyme is immobolized may be treated with the basic amino acid by bringing said carrier surface into contact with the solution of basic amino acid. This may be realized by causing the solution of basic amino acid to flow on to the carrier surface or by immersing the carrier within the solution of basic amino acid. A preferred temperature at which the surface of the carrier on which the fibrinolytic enzyme is immobilized is brought into contact with the solution of basic amino acid ranges from about 0° to about 50° C. If desired, agitation or shaking may be used to promote contact between the carrier surface and the solution of basic amino acid.

The carrier on which the fibrinolytic enzyme stabilized by the method of the present invention is immobilized may be sterilized by a variety of methods including the use of sterilizing gases such as ethylene oxide, propylene oxide, formaldehyde, $\beta$-propiolactone and methyl bromide, and the use of radiations such as X-rays, electromagnetic radiations, accelerated electron beams, beta-rays, alpha-rays, and particulate radiations (e.g., neutrons and protons). The pressure and temperature of the sterilizing gas, as well as the dose and duration of irradiation may be properly selected depending upon the number of microbes adhering to the carrier on which the fibrinolytic enzyme is immobilized. The sterilizing container may be of any type that is permeable to the sterilizing gas used but is non-permeable to microbes, or which is transparent to sterilizing radiations. The container need not be in a bag form and may assume any other forms such as a tube and a box.

In accordance with the present invention, the time-dependent stability of the immobilized fibrinolytic enzyme can be significantly enhanced while at the same time, the enzyme can be rendered appreciably resistant against deactivation that will otherwise occur as a result of sterilization.

The following examples are provided for further illustrating the advantages of the present invention. In the examples, fibrinolytic activity measurement was conducted in accordance with the method described in *Rinsho Kensaho Teiyo* (Manual of Clinical Testing), ed. by Kanai, Kanai, rev. 27th ed., VI-110, Kanehara Shuppan: i.e., a sample was put on a fibrin plate prepared from a mixture of an aqueous human fibrinogen solution and a solution of thrombin in physiological saline, and after leaving the sample to stand at 37° C. for 24 hours, the diameter and the length of minor axis of the plaque forming around the sample by fibrinolysis were measured, to indicate the degree of fibrinolysis in terms of (diameter) x (length of minor axis) in mm$^2$.

EXAMPLE 1

A circular (5 mm$\phi$) film (thickness: 120 $\mu$m) of aminoacetal-modified polyvinyl alcohol (with 5.2 mol% of aminoacetal) was immersed in a 5 wt% acetone solution of ethylene-maleic anhydride copolymer at room temperature for 5 hours. The film was then recovered from the solution, washed with acetone and dried. The dried film was immersed in a physiological saline solution of urokinase (600 U/ml) at 7° C. for 24 hours, recovered therefrom, and washed with sterilized distilled water. The washed film was immersed in a 0.01 wt% aqueous solution of histidine at room temperature for 5 minutes, recovered therefrom, and dried.

The activity of urokinase immobilized in the histidine treated film was 576 mm$^2$: the film formed a circular plaque (24 mm$\phi$) by lysing the fibrin.

As a control, the activity of urokinase immobilized in a histidine-untreated film and was also 576 mm$^2$.

The two films were left in incubators at two different temperatures, 60° C. and 30° C., both at the same relative humidity, viz., 55%. The film stability at the respective temperatures is shown in Table 1 below.

TABLE 1

| Temperature | Histidine Treatment | Immediately after Immobilization (mm²) | 1 Day (mm²) | 3 Days (mm²) | 6 Days (mm²) | 10 Days (mm²) |
|---|---|---|---|---|---|---|
| 30° C. | yes | 576 | 600 | 575 | 576 | 576 |
| 30° C. | no | 576 | 576 | 575 | 529 | 506 |
| 60° C. | yes | 576 | 600 | 576 | 552 | 552 |
| 60° C. | no | 576 | 575 | 529 | 462 | 380 |

Comparative Example 1

The procedures of Example 1 were repeated, except that histidine was replaced by glycine, which, according to Japanese Patent Application (OPI) No. 142593/1978, was as effective as lysine and arginine in stabilizing the activity of a urokinase solution. The activity of the urokinase immobilized in the glycine-treated film was measured as in Example 1. The results are shown in Table 2 together with the data glycine-untreated control sample.

TABLE 2

| Temperature | Glycine Treatment | Immediately after Immobilization (mm²) | 1 Day (mm²) | 3 Days (mm²) | 6 Days (mm²) | 10 Days (mm²) |
|---|---|---|---|---|---|---|
| 30° C. | yes | 602 | 520 | 475 | 270 | 204 |
| 30° C. | no | 576 | 576 | 575 | 529 | 506 |
| 60° C. | yes | 602 | 320 | 182 | 75 | 32 |
| 60° C. | no | 576 | 575 | 529 | 462 | 380 |

The above data show that glycine, conventionally included within the group of lysine and arginine as a stabilizer for the activity of urokinase in solution, is entirely ineffective with immobilized urokinase, and rather accelerates its deactivation.

EXAMPLE 2

A circular (5 mmφ) film (150 μm thick) of polyurethane was immersed in an acetone solution of maleic anhydride-methyl vinyl ether copolymer (2 wt/v%) and polyethylene glycol (1 wt/v%, mol. wt. 400) at room temperature for 30 seconds and heated at from 90° to 100° C. for 2 hours in vacuuo. The film was immersed in a physiological saline solution of urokinase (600 U/ml) at 7° C. for 24 hours, recovered therefrom and washed with sterilized distilled water. The washed film was immersed in an aqueous solution of a mixture of arginine (0.01 wt%) and histidine (0.01 wt%) at room temperature for 2 minutes, recovered therefrom, and dried.

A test was conducted to examine the stability of the urokinase immobilized in the treated polyurethane film at room temperature (25° C.). The same test was conducted with an arginine and histidine-untreated polyurethane film in which urokinase was immobilized. The results are shown in Table 3.

TABLE 3

| Treatment with Arginine and Histidine | Immediately after Immobilization (mm²) | 1 Month (mm²) | 3 Months (mm²) | 6 Months (mm²) | 12 Months (mm²) |
|---|---|---|---|---|---|
| yes | 600 | 625 | 600 | 600 | 576 |
| no | 600 | 552 | 484 | 400 | 361 |

The two types of polyurethane film were left in incubators at different temperatures, 60° C. and 30° C., at the same relative humidity, viz., 55%, in order to examine the stability of urokinase at the respective temperatures. The results are shown in Table 4.

TABLE 4

| Temperature | Treatment with Arginine and Histidine | Immediately after Immobilization (mm²) | 1 Day (mm²) | 3 Days (mm²) | 6 Days (mm²) | 10 Days (mm²) |
|---|---|---|---|---|---|---|
| 30° C. | yes | 600 | 602 | 600 | 598 | 600 |
| 30° C. | no | 600 | 600 | 599 | 551 | 527 |
| 60° C. | yes | 600 | 600 | 588 | 571 | 563 |
| 60° C. | no | 599 | 599 | 551 | 481 | 396 |

The two types of film were put into polyethylene bags (thickness of 40μ; product of Hogi), which were then completely sealed and exposed to radiation from Co-60 to give a total dose of 2.5 Mrad. The activity of urokinase in each of the sterilized bags was measured and the results are shown in Table 5. Each film was found to be germ-free.

TABLE 5

| Treatment with Arginine and Histidine | Immediately after Immobilization (mm²) | After Sterilization (mm²) | Residual Activity (%) |
|---|---|---|---|
| yes | 600 | 576 | 96.0 |
| no | 600 | 361 | 60.2 |

Comparative Example 2

The procedures of Example 2 were repeated, except that the aqueous solution of a mixture of arginine (0.01 wt%) and histidine (0.01 wt%) was replaced by a 0.02 wt% aqueous solution of threonine, which, according to Japanese Patent Application (OPI) No. 147916/1979, is as effective as arginine and histidine when used in combination with human serum albumin for the purpose of stabilizing urokinase injections.

A test was conducted as in Example 2 to determine the stability of urokinase immobilized in the threonine-treated film at 60° C. and 30° C. The results are shown in Table 6 together with data for urokinase on a threonine-untreated film.

TABLE 6

| Temperature | Treatment with Threonine | Immediately after Immobilization (mm²) | 1 Day (mm²) | 3 Days (mm²) | 6 Days (mm²) | 10 Days (mm²) |
|---|---|---|---|---|---|---|
| 30° C. | yes | 565 | 550 | 542 | 533 | 500 |
| 30° C. | no | 576 | 576 | 575 | 529 | 506 |
| 60° C. | yes | 565 | 548 | 520 | 453 | 391 |
| 60° C. | no | 576 | 575 | 529 | 462 | 380 |

The above data show that threonine which, when combined with human serum albumin, is conventionally regarded as being effective in stabilizing urokinase in solution, is substantially ineffecitive for the purpose of stabilizing immobilized urokinase.

The two types of film were put into sterilizing bags (product having one surface of polyethylene film and another surface of polyethylene nonwoven material, product of Hogi) which were completely sealed and sterilized by a mixture of ethylene oxide gas (20%) and $CO_2$ (80%) that was supplied at a pressure of 1 kg/cm²G (40° C. ×40% r.h.) for 2 hours.

The residual activity of urokinase in each of the sterilized bags was determined and the results are shown in Table 7.

TABLE 7

| Treatment with Threonine | Immediately after Immobilization (mm$^2$) | After Sterilization (mm$^2$) | Residual Activity (%) |
|---|---|---|---|
| yes | 565 | 325 | 57.6 |
| no | 576 | 342 | 59.4 |

The above data show that threonine is also ineffective in preventing the activity of immobilized urokinase from being reduced as a result of sterilization.

EXAMPLE 3

A commercial CNBr-Sepharose resin (Pharmacia Fine Chemicals) was washed several times with 1 mM HCl. The resin was immersed in a physiological saline solution of streptokinase (600 U/ml) at 4° C. for 24 hours, recovered therefrom and washed with sterilized distilled water. The washed resin was immersed in a 0.02 wt% aqueous solution of arginine at room temperature for 2 minutes, recovered therefrom and dried with air.

A test was conducted to determine the stability of streptokinase in the resin at 60° C. as one tablet of the latter was placed on a fibrin plate. The same test was conducted with an untreated resin. The results are shown in Table 8.

TABLE 8

| Treatment with Arginine | Immediately after Immobilization (mm$^2$) | 1 Day (mm$^2$) | 3 Days (mm$^2$) | 6 Days (mm$^2$) | 10 Days (mm$^2$) |
|---|---|---|---|---|---|
| yes | 110 | 121 | 99 | 110 | 99 |
| no | 110 | 100 | 90 | 81 | 64 |

One gram each of the two resins was put into a sterilizing bag (product having one surface of polyethylene film and another surface of polyethylene nonwoven material, product of Hogi), which was completely sealed and then sterilized with a mixture of ethylene oxide gas (20%) and CO$_2$ (80%) that was supplied at 1 kg/cm$^2$G (40° C.×40% r.h.) for 2 hours. The activity of the sterilized streptokinase in each bag was determined, with one tablet of the resin placed on a fibrin plate. The results are shown in Table 9. Each of the resins was found to be germ-free.

TABLE 9

| Treatment with Arginine | Immediately after Immobilization (mm$^2$) | After Sterilization (mm$^2$) | Residual Activity (%) |
|---|---|---|---|
| yes | 110 | 108 | 98.2 |
| no | 110 | 64 | 58.2 |

EXAMPLE 4

The procedures of Example 1 were repeated except that histidine was replaced by arginine. The activity of urokinase immobilized on the arginine-treated film was 576 mm$^2$: the film formed a circular plaque (24 mm$\phi$) by lysing the fibrin. As a control, urokinase was immobilized on an arginine-untreated film and its fibrinolytic activity was also 576 mm$^2$.

The two films were individually put in a sterilizing bag (product having one surface of polyethylene film and another surface of polyethylene nonwoven material, product of Hogi) which was completely sealed and sterilized with a mixture of ethylene oxide gas (20%) and CO$_2$ (80%) that was supplied at 1 kg/cm$^2$G (40° C.×40% r.h.) for 2 hours. The activity of urokinase in each of the sterilized bags was measured and the results are shown in Table 10. Both films were found to be germ-free.

TABLE 10

| Treatment with Arginine | Immediately after Immobilization (mm$^2$) | After Sterilization (mm$^2$) | Residual Activity (%) |
|---|---|---|---|
| yes | 576 | 575 | 99.8 |
| no | 576 | 342 | 59.4 |

While the invention has been described in detail and with reference to specific embodiments thereof, it will be apparent to one skilled in the art that various changes and modifications can be made therein without departing from the spirit and scope thereof.

What is claimed is:

1. A method for stabilizing an immobilized fibrinolytic enzyme, comprising contacting the surface of a carrier containing said enzyme immobilized thereon, with a basic amino acid selected from the group consisting of histidine, arginine and lysine.

2. A method according to claim 1, wherein said basic amino acid is histidine.

3. A method according to claim 1, wherein said basic amino acid is arginine.

4. A method according to claim 1, wherein the surface of the carrier is contacted with a solution containing basic amino acid in a range of from about 0.00001 wt% to about 30 wt%.

5. A method according to claim 2, wherein the surface of the carrier is contacted with a solution containing histidine in a range of from about 0.00001 wt% to about 30 wt%.

6. A method according to claim 3, wherein the surface of the carrier is contacted with a solution containing arginine in a range of from about 0.00001 wt% to about 30 wt%.

7. A method according to claim 1, wherein the surface of the carrier is contacted with a solution containing basic amino acid in a range of from 0.001 wt% to 1 wt%.

8. A method according to claim 2, wherein the surface of the carrier is contacted with a solution containing histidine in a range of from 0.001 wt% to 1 wt%.

9. A method according to claim 3, wherein the surface of the carrier is contacted with a solution containing arginine in a range of from 0.001 wt% to 1 wt%.

10. A method according to claim 1, wherein the contacting is carried out at a temperature of from about 0° to about 50° C.

11. A method according to claim 4, wherein the contacting is carried out at a temperature of from about 0° to about 50° C.

12. A method according to claim 11, wherein said basic amino acid is histidine.

13. A method according to claim 11, wherein said basic amino acid is arginine.

14. A method according to claim 7, wherein the contacting is carried out at a temperature of from about 0° to about 50° C.

15. A method according to claim 14, wherein said basic amino acid is histidine.

16. A method according to claim 14, wherein said basic amino acid is arginine.

* * * * *